United States Patent [19]

Tuttle

[11] 4,454,142

[45] Jun. 12, 1984

[54] HYPERKINETIC CHILD TREATMENT AGENT

[75] Inventor: Ronald R. Tuttle, Miami, Fla.

[73] Assignee: Key Pharmaceuticals, Inc., Miami, Fla.

[21] Appl. No.: 479,639

[22] Filed: May 26, 1983

[51] Int. Cl.$^3$ .......................................... A61K 31/485
[52] U.S. Cl. .................................................... 424/260
[58] Field of Search ........................................ 424/260

[56] References Cited

PUBLICATIONS

J. Med. Chem. 18, No. 3 (259–269)(1975).

Primary Examiner—Stanley J. Friedman
Attorney, Agent, or Firm—Wegner & Bretschneider

[57] ABSTRACT

Provided is a method of orally treating a child having a tendency to be overactive to the extent of requiring an external control which comprises orally administering to said child a pharmaceutically effective amount of 6-methylene-6-desoxy-N-cyclopropylmethyl-14-hydroxydihydronormorphone to said patient, whereby the patient tends to reduce his food intake.

4 Claims, No Drawings

HYPERKINETIC CHILD TREATMENT AGENT

In accordance with a first aspect of the invention there is provided a method of orally treating a child having a tendency to be overactive to the extent of requiring an external control which comprises orally administering to said child a pharmaceutically effective amount of 6-methylene-6-desoxy-N-cyclopropylmethyl-14-hydroxydihydronormorphone to said patient, whereby the patient tends to reduce his food intake. Preferably, the administration is once or twice daily, although shorter intervals of delivery are possible. The dosage is calculated on a basis that the pharmaceutically acceptable amount is at from about 5 to about 75 mg per day based upon a normal child's body weight, which is taken as 30 kg.

Although a parent is usually present at breakfast and dinner so that a dosage administration can be monitored at such times, this is not always possible at luncheon, whereby a sustained release form that permits administration of the medication only at breakfast and dinner is contemplated in a preferred aspect of the invention. According it is contemplated that there be provided an oral sustained release dosage unit form suitable for treating a child having a tendency to be overactive to the extent of requiring an external control, said oral sustained release dosage unit form permitting a prolonged interval between administration to said patient, said oral doage unit formulation comprising a plurality of granules which together constitute a pharmaceutically effective amount of 6-methylene-6-desoxy-N-cyclopropylmethyl-14-hydroxydihydronormorphone to provide a sustained action, said plurality of granules each comprising a polymeric matrix to permit a substantially even release of said 6-methylene-6-desoxy-N-cyclopropylmethyl-14-hydroxydihydronormorphone to permit the necessary sustained release over the prolonged period of time. This oral sustained release dosage unit form may be a tablet compressed of said plurality of granules, optionally including a flavoring agent such as L-aspartyl-L-phenylalanine. Alternatively, the oral sustained release dosage unit form may be a capsule containing said plurality of granules. It is recognized in the scientific community that there are negative side effects with the traditionally used amphetamines. Studies are now being conducted on various opiate receptors. 6-methylene-6-desoxy-N-cyclopropylmethyl-14-hydroxydihydronormorphone provides an excellent form for oral administration, which is not feasible for certain other opioid receptors such as naloxone.

The total daily dosage per child ("child"=30 kg) will of course vary dependent upon the weight of the patient, but calculated upon the weight of the child, and will normally be from about 5 to about 75 mg per day is contemplated, and still more preferably about 15 to about 35 mg per day. Preferably, it is contemplated that a dosage would be about 25 mg per day.

A sustained release dosage unit form is provided for 6-methylene-6-desoxy-N-cyclopropylmethyl-14-hydroxydihydronormorphone to release the agent over a prolonged period of at least about eight, and preferably at least about 12 hours, to permit a patient to typically take one oral sustained release dosage form before breakfast, for example, when taking orange juice or other breakfast drink, and just before dinner. In a preferred embodiment, the oral dosage unit form is a tablet, but other sustained release forms are also contemplated, for example, capsules or spanules may also be used. As a preferred oral dosage unit form may be mentioned a plurality of granules each of which contains an essentially uniform distribution of the pharmaceutically active ingredient, the 6-methylene-6-desoxy-N-cyclopropylmethyl-14-hydroxydihydronormorphone, contained in a sustained release vehicle, which sustained release vehicle releases the 6-methylene-6-desoxy-N-cyclopropylmethyl-14-hydroxydihydronormorphone over a prolonged period of time whereby the possibility of infrequent, preferably not more than twice a day, dosing is achieved. As the sustained release vehilcle may be mentioned a mixture of cellulosic polymers such as hydroxypropyl methylcellulose typically having a molecular weight of from about 20,000 to about 140,000 which may be advantageously mixed with polyvinylpyrrolidone having a molecular weight of about 20,000 to about 100,000, and preferably about 40,000. When polyvinylpyrrolidone is used it is preferably used in an amount of from about 0.2 to about 0.5 parts per unit of cellulosic polymer.

A total dosage of from about 2 to about 25 mg per oral sustained release dosage unit is contemplated. In a preferred embodiment where the oral sustained release dosage unit is to be delivered on a once per 12 hour basis the total quantity of 6-methylene-6-desoxy-N-cyclopropylmethyl-14-hydroxydihydronormorphone per dosage unit form is from about 7 to about 20 mg, and still more preferably about 12 mg. It is contemplated that the dosage unit formulation include at least about 200 and preferably at least about 400 of the granules per dosage unit, and not more than about 1500 granules per dosage unit formulation. The use of about 600 such granules is contemplated in a preferred embodiment.

When the oral dosage unit formulation is to be in the form of a tablet, the granules are mixed together with typical tableting excipients, for example, about 1% magnesium stearate. In a further variation of the present invention, there may also be included a minor amount, typically not more than about 3% of the total weight, of a flavoring agent. This flavoring agent may be based upon a sweetener which is essentially devoid of significant caloric value. In this variation, there is included in the mixture adding the tableting excipient preferably about 0.2 to about 1% of the tablet weight, be comprised of a sweetener without significant caloric value, for example, saccharine or L-aspartyl-L-phenylalanine.

As an alternative embodiment to the tablet as the oral dosage unit formulation may be mentioned a capsule, which would simply include the necessary plurality of granules that would be released into the gastrointestinal tract upon the dissolution of the capsule.

A rectal suppository is also contemplated as an alternate sustained release vehicle, in which case a wax vehicle is contemplated for the sustained release of the 6-methylene-6-desoxy-N-cyclopropylmethyl-14-hydroxydihydronormorphone over the desired prolonged period of time.

While 6-methylene-6-desoxy-N-cyclopropylmethyl-14-hydroxydihydronormorphone has been referred to as the active ingredient of the present invention, it is contemplated that any pharmaceutically acceptable salt form may be used, and it is preferred that the hydrochloride be used in formulations unless otherwise specified. Other forms derived from 6-methylene-6-desoxy-N-cyclopropylmethyl-14-hydroxydihydronormorphone may also be used and are specifically considered to be within the scope of the invention.

The following examples serve to illustrate the invention:

EXAMPLE I

Mixed together are 23 gm 6-methylene-6-desoxy-N-cyclopropylmethyl-14-hydroxydihydronormorphone; 140 gm polyvinylpyrrolidone (mw 40,000); and 250 gm hydroxypropylmethylcellulose (mw=120,000, Methocel K15M, Dow Chemical). The blend which results from this mixture is granulated with 160 ml deionized water to produce granules which are then dried at a temperature of 50° C., followed by grinding. The sufficiently small granules which are obtained by passing the mixture of granules through a 14 mesh screen are then lubricated with 5 mg magnesium stearate, and tablets having a total weight of 500 mg are thereafter compressed from this mixture.

EXAMPLE II

By following the procedure set froth in Example II, but adding 4 mg L-aspartyl-L-phenylalanine together with the addition of the 5 mg magnesium stearate, a sweetened tablet is obtained without significant caloric value.

What is claimed is:

1. A method of orally treating a child having a tendency to be overactive to the extent of requiring an external control which comprises orally administering to said child a pharmaceutically effective amount of 6-methylene-6-desoxy-N-cyclopropylmethyl-14-hydroxydihydronormorphone to said patient, whereby the patient tends to reduce his food intake.

2. A method of claim 1 wherein said periodic oral delivery is at least once per day.

3. A method of claim 2 wherein said periodic oral delivery is at least twice per day.

4. A method of claim 1 wherein said pharmaceutically acceptable amount is at from about 5 to about 75 mg per day based upon a normal child's body weight.

* * * * *